United States Patent [19]

Shimizu et al.

[11] Patent Number: 4,855,518

[45] Date of Patent: Aug. 8, 1989

[54] METHOD FOR PRODUCING P-ALKYLSTYRENE

[75] Inventors: Isoo Shimizu; Yuuichi Tokumoto, both of Yokohama, Japan

[73] Assignee: Nippon Petrochemicals Company, Limited, Japan

[21] Appl. No.: 221,119

[22] Filed: Jul. 19, 1988

[30] Foreign Application Priority Data

Jul. 22, 1987 [JP] Japan ................... 62-183001

[51] Int. Cl.$^4$ .............................. C07C 4/24
[52] U.S. Cl. ..................... 585/319; 585/320; 585/321; 585/426; 585/439; 585/446; 585/456
[58] Field of Search ............... 585/319, 320, 321, 439, 585/426, 446, 454

[56] References Cited

U.S. PATENT DOCUMENTS

| | | | |
|---|---|---|---|
| 3,062,903 | 11/1962 | Odioso et al. | 585/439 |
| 3,441,625 | 4/1969 | Bargeron et al. | 585/439 |
| 4,070,366 | 1/1978 | Gregorovich et al. | 585/454 |
| 4,694,100 | 9/1987 | Shimizu et al. | 560/105 |

Primary Examiner—Curtis R. Davis
Attorney, Agent, or Firm—Scully, Scott, Murphy & Presser

[57] ABSTRACT

A method for producing p-alkylstyrene which is characterized in that side reaction scarcely occurs, catalyst and unreacted material are easily recovered for the reuse, the p-position selectivity is excellent and yield of aimed product is high. In the method, monoalkylbenzene having an alkyl group with 3 or more carbon atoms is reacted with acetaldehyde in the presence of hydrogen fluoride catalyst under the conditions of a temperature of 0° C. or lower, a molar ratio of 2 to 100 in "alkylbenzene/acetaldehyde", the other molar ratio of 1.7 to 300 in "hydrogen fluoride/acetaldehyde", the proportion of hydrogen fluoride to the sum of hydrogen fluoride and water in the reaction system of 65% by weight or higher, and the concentration of acetaldehyde in the reaction system of 1.0% by weight or lower to obtain 1,1-bis(p-alkylphenyl)ethane, and then subjecting it to catalytic cracking at a temperature in the range of 200° to 650° C. in the presence of an acid catalyst.

6 Claims, No Drawings

METHOD FOR PRODUCING P-ALKYLSTYRENE

BACKGROUND OF THE INVENTION

1. Field of the Invention

This invention relates a method for producing alkyl-substituted styrene, preferably p-alkylstyrene, having an alkyl substituent group with 3 or more carbon atoms from monoalkylbenzene through 1,1-bis(p-alkylphenyl)ethane.

2. Description of the Prior Art

It is well known that 1,1-bis(p-alkylphenyl)ethane can be converted into p-alkylstyrene in a high yield by means of catalytic cracking. There are hitherto proposed several methods to synthesize 1,1-bis(p-alkylphenyl)ethane. As one of them, there is proposed a method that p-isobutylbenzene is reacted with acetaldehyde in the presence of sulfuric acid catalyst to obtain 1,1-bis(p-isobutylphenyl)ethane (U.S. Pat. No. 4,694,100).

When isobutylbenzene is used as a monoalkylbenzene as described in the above patent specifications, 1,1-bis(p-isobutylphenyl)ethane is obtained, which is especially used as an intermediate compound for economically preparing ibuprofen (tradename) that is effective as a medicine for the relief of inflammation.

As described in the above patent specifications, however, the sulfonation of valuable isobutylbenzene itself cannot be avoided owing to the use of sulfuric acid. As a result, a part of isobutylbenzene is lost in the form of sulfonation product, which is not desirable in view of economy.

Furthermore, because this reaction is dehydration, the concentration of sulfuric acid as a catalyst is lowered with the progress of reaction due to released water. Therefore, in order to reuse the sulfuric acid, it is necessary to recover the concentration of used sulfuric acid by a method such as high-temperature distillation in which the corrosion of apparatus is apprehended. In addition, the recovery of the catalyst concentration is not easy by a measure of mere distillation because much sulfonation product is dissolved in the sulfuric acid phase.

More particularly, it is known that p-alkylstyrene is obtained in a good yield by catalytically cracking symmetric 1,1-bis(p-alkylphenyl)ethane (foregoing United States Patent). However, it has been difficult to obtain inexpensively the raw material of 1,1-bis(p-alkylphenyl)ethane.

For example, in a method to prepare 1,1-bis(p-alkylphenyl)ethane by reacting monoalkylbenzene with acetaldehyde in the presence of concentrated sulfuric acid, monoalkylbenzene sulfonic acid that is the sulfonation product of the starting alkylbenzene is produced by side reaction. Therefore, the loss of the starting alkylbenzene is not negligible. Furthermore, for the reuse of sulfuric acid catalyst containing much organic sulfonic acid, the concentration of sulfuric acid which was lowered by the generation of water during the reaction must be recovered. However, the method such as distillation in which heat is applied cannot be adopted because the corrosion by hot sulfuric acid is severe. Accordingly, it was necessary to remove the generated water by chemical reaction with adding sulfuric anhydride or fuming sulfuric acid, which increased the cost of catalyst.

On the other hand, when monoalkylbenzene is reacted with acetaldehyde in the presence of hydrogen fluoride catalyst, it is desirable that the side reaction to produce sulfonated product does not occur. However, in accordance with the experiments of the present inventors, when monoalkylbenzene was condensed in the presence of hydrogen fluoride catalyst, it was confirmed that a by-product of p-monoalkylethylbenzene was produced, which is of course undesirable because the by-product causes the loss of material. It is, therefore, required to reduce as far as possible both the loss of raw materials and the side reaction to form p-alkylethylbenzene.

The carbon number of alkyl group in the by-produced p-monoalkylethylbenzene is the same as the carbon number of alkyl group in the starting material of alkylbenzene.

Incidentally, in the case that the number of carbon atoms of the alkyl groups of the by-product of alkylethylbenzenes is less than 3, the dehydrogenated products obtained by dehydrogenating these compounds are all alkylstyrenes, which are nothing but the aimed compounds in the present invention.

Accordingly, if the by-product is dehydrogenated, it may be used effectively and there occurs no disadvantage when an alkylbenzene having an alkyl group with less than 3 carbon atoms is used as a raw material. In addition, the dehydrogenation can be carried out easily.

From such a viewpoint, when a monoalkylbenzene having a substituent chain with less than 3 carbon atoms is used as a starting material for preparing alkylstyrene, there is no use in paying consideration to the generation of the above-mentioned by-product. The reason is that the by-product of alkylethylbenzene such as diethylbenzene and methylethylbenzene can be easily dehydrogenated into the aimed compound of alkylstyrene, and therefore, the by-product is by no means the loss in process.

On the other hand, when the alkylethylbenzene as a by-product which is obtained by using a starting material of monoalkylbenzene having a substituent group with 3 or more carbon atoms, is dehydrogenated, there is a possibility that the alkyl group with 3 or more carbon atoms as well as ethyl group of the alkylethylbenzene are dehydrogenated together. Accordingly, the dehydrogenation products are naturally a mixture of plural kinds of styrene derivatives. What is worse, they cannot be separated easily by ordinary distillation because the molecular weights of them are close to one another. Therefore, the effective use of the by-product of alkylethylbenzene is not possible, which reduces the yield of alkylstyrene corresponding to the quantity of the formed by-product.

In view of the effective use of the by-product, the use of a starting material of such an alkylbenzene having a substituent group with 3 or more carbon atoms, is not desirable. It is, therefore, necessary to suppress the formation of the by-product of this kind.

For the above reason, when a starting material of monoalkylbenzene having a substituent group with 3 or more carbon atoms is used, it is especially necessary to suppress the formation of the by-product of alkylethylbenzene.

In U.S. Pat. No. 3,002,034, a method of reaction with hydrogen fluoride catalyst is referred to. However, in all the reactions described in examples, a raw material of toluene and a catalyst of sulfuric acid are used, while any practical investigation on the reaction using hydrogen fluoride is not made. In view of the description that the reaction temperature is 5° C. or above, preferably 15° to 60° C., the disclosure basically relates to the art to use sulfuric acid as a catalyst. Therefore, the reference teaches nothing with respect to the present invention. In addition, it is described in Example IV of the same reference that the by-product is a high boiling material which is believed to be tetramethyldihydroanthracene and, in Example V to VII, the formation of high boiling polymer is recognized. These examples are all carried out with sulfuric acid catalyst. From these facts, it can be naturally supposed that the kinds and quantities of by-products are varied according to the kind of catalyst.

It is, therefore, the object of the present invention to produce p-alkylstyrene with avoiding the loss in the form of sulfonation products, to suppress the formation of the by-product of alkylethylbenzene as low as possible, and as a result, to reduce the loss of the raw material of alkylbenzene.

BRIEF SUMMARY OF THE INVENTION

The present invention relates to a method for producing p-alkylstyrene from a monoalkylbenzene and acetaldehyde through 1,1-bis(p-alkylphenyl)ethane.

The process of the invention is represented by the following chemical equations:

(1) Condensation

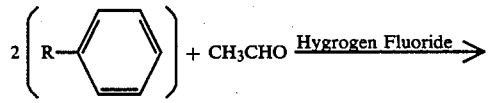

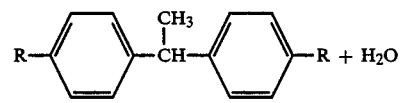

(2) Catalytic Cracking

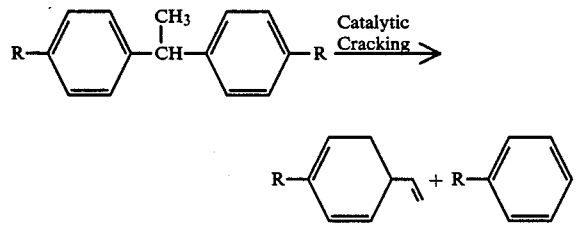

wherein R is an alkyl group having 3 or more carbon atoms.

More particularly, the present invention relates to a method for economically producing substituted styrene having an alkyl substituent group with 3 or more carbon atoms on p-position (p-alkylstyrene) which is characterized in that a monoalkylbenzene is firstly reacted with acetaldehyde in the presence of hydrogen fluoride catalyst to obtain 1,1-bis(p-alkylphenyl)ethane and it is then catalytically cracked in the presence of an acid catalyst.

DETAILED DESCRIPTION OF THE INVENTION

The monoalkylbenzene used in the method of the present invention is a mono-substituted benzene having an alkyl substituent group with 3 or more, preferably 4 or more, carbon atoms. For example, they are propylbenzene, isopropylbenzene, n-butylbenzene, isobutylbenzene, and t-butylbenzene. In view of reactivity, monoalkylbenzenes having a substituent group with 10 or less carbon atoms are generally used. Among them, isobutylbenzene is especially preferable.

In the condensation reaction of the present invention, the concentration of the catalyst of hydrogen fluoride is maintained 65% by weight or higher, preferably 75% by weight or higher, with regard to the total quantity of the hydrogen fluoride and water in the reaction system. The concentration thus specified will be hereinafter referred to as "aqueous hydrogen fluoride concentration".

In the case that the aqueous hydrogen fluoride concentration in the reaction system is lower than 65% by weight, the yield of 1,1-bis(p-alkylphenyl)ethane is low and the by-product of alkylethylbenzene is generated, in addition, the formation of polymeric substances increases, in which the object of the present invention cannot be attained effectively.

As will be understood from the foregoing chemical equation, this reaction is dehydration. Accordingly, water is generated with the progress of reaction to lower the aqueous hydrogen fluoride concentration in the reaction mixture.

In order to maintain the level of aqueous hydrogen fluoride concentration in the water generating reaction, it is possible to supply the reaction system continuously with gaseous hydrogen fluoride or aqueous hydrogen fluoride. The concentration of aqueous hydrogen fluoride to be fed so as to maintain the aqueous hydrogen fluoride concentration is desirably 80% by weight or higher. If the concentration of the aqueous hydrogen fluoride to be fed is lower than 80% by weight, it is not economical because the necessary feed quantity much increases.

The use quantity of hydrogen fluoride is 1.7 to 300 times by mole, preferably 2.7 to 100 times by mole with respect to the feed of acetaldehyde. If the quantity of hydrogen fluoride is less than 1.7 times by mole, it is not desirable because much by-product of alkylethylbenzene is generated. On the other hand, if the quantity of hydrogen fluoride exceeds 300 times by mole, it is uneconomical because any additional advantage cannot be expected by the excess addition. It is understood that fluorides, which may be by-produced, are generally dissolved in the phase of hydrogen fluoride. However, in comparison with the use of sulfuric acid catalyst, when hydrogen fluoride catalyst is used, organic fluorides dissolved into hydrogen fluoride phase is not more than 1% and the loss of alkylbenzene is scarcely caused to occur. In addition, hydrogen fluoride can be recovered without difficulty by distillation at a level near room temperature and the recovered hydrogen fluoride intact can be used again for the reaction.

As the material to be reacted with monoalkylbenzene besides acetaldehyde itself, paraldehyde of a trimer of acetaldehyde or else can also be used. Of course, the quantities of them must be taken on basis of acetaldehyde-unit.

In the reaction according to the present invention, it is inevitable that the concentration of acetaldehyde in the reaction system is maintained at 1.0% by weight or lower, preferably lower than 0.5% by weight. If the concentration of acetaldehyde is higher than this value, the reaction is liable to stop halfway. As a result, the quantity of intermediate substance increases and side reaction such as polymerization of acetaldehyde is caused to occur to reduce the yield, which are not desirable.

As the monoalkylbenzenes, any of those which are prepared by conventionally known methods can be used. Without saying, pure compounds can be used and those which are diluted by or dissolved in an aliphatic hydrocarbon such as pentane or hexane can also be used.

The use quantity of monoalkylbenzene is generally excess amount relative to the quantity of acetaldehyde, for instance, 2 times by mole, preferably 2.2 times by mole or more. The quantity of monoalkylbenzene less than the above value is not desirable because an effective reaction cannot be attained and the by-product of alkylethylbenzene and polymeric substances are formed. The upper limit of the use quantity of monoalkylbenzene is determined mainly from the viewpoint of economy and, in practice, the quantity is, for example, not more that 100 times by mole, preferably less than 50 times by mole.

In the preparation of 1,1-bis(p-alkylphenyl)ethane, it is necessary that the reaction temperature is maintained at a level not higher than 0° C., preferably below $-5°$ C. with sufficient stirring. The reaction at a temperature above 0° C. is not desirable because the by-product of alkylethylbenzene is generated and, in addition, side reaction such as polymerization abruptly increases. Accordingly, it is desirable that a reaction vessel is cooled internally or externally. The reaction temperature is maintained preferably as low as possible and there is no lower limit of the reaction temperature. However, the lower limit of the reaction temperature may be determined appropriately taking the freezing of reaction products into consideration. This lower limit of reaction temperature is generally $-60°$ C.

In a desirable reaction system, monoalkylbenzene as one of reactants and hydrogen fluoride of a certain concentration are fed into a reaction vessel and the reaction is carried out with supplying a certain amount of acetaldehyde or its solution of monoalkylbenzene little by little with maintaining the reaction temperature at a certain value. At the same time, hydrogen fluoride of a concentration which is higher than that of the hydrogen fluoride in the reaction mixture, is added to the reaction system so as to maintain the concentration of hydrogen fluoride in the reaction system.

A long time operation is not always necessary because the rate of reaction of the present invention is relatively high. The necessary time length of the reaction is preferably in the range of 0.1 to 10 hours.

In connection with the pressure of reaction, there is no special limitation so long as the reaction phase is maintained in liquid state. The reaction is preferably carried out under atmospheric pressure or autogenous pressure at a reaction temperature in a sealed reaction vessel.

After the reaction, the stirring is stopped and hydrogen fluoride is removed from the reaction mixture. The hydrogen fluoride can be distilled off quite easily by low temperature distillation or else which is different from the case of sulfuric acid catalyst. After distilling off the hydrogen fluoride, the remaining acidic contents are neutralized by an alkali such as sodium hydroxide, potassium hydroxide, calcium hydroxide or sodium carbonate or their solutions, which is followed by water rinsing. In this step, it is possible to add a solvent such as ether or n-hexane in order to avoid emulsifying.

After the neutralization, a hydrocarbon layer is separated and preferably it is distilled under reduced pressure to obtain unreacted monoalkylbenzene and 1,1-bis(p-alkylphenyl)ethane. In the method of the present invention, the isomerization of the side chain alkyl groups of the unreacted monoalkylbenzene does not occur at all. Therefore, the unreacted alkylbenzene recovered by distillation can be reused by recycling it without applying any special refining treatment.

When a mixture containing position isomers is catalytically cracked, obtained alkylstyrene is undesirably a mixture of position isomers. However, by employing the above-mentioned condensation process of the present invention, it is convenient that the highly pure 1,1-bis(p-alkylphenyl)ethane can be used as a raw material.

In the catalytic cracking according to the present invention, the contact with an acid catalyst is preferably carried out under a diluted condition with the coexistence of an inert gas. So long as an inert gas does not impair the acidic activity of an acid catalyst, any of methane, ethane and propane as well as inorganic inert gases such as hydrogen, helium, argon, nitrogen and steam can be used. The inert gas may be used singly or in a suitable mixture. From an industrial viewpoint, steam is preferable in handling as an inert gas. The dilution with an inert gas is preferably carried out such that the molar ratio represented by "inert gas/1,1-bis(p-alkylphenyl)ethane" is 50 or higher. There is no upper limit of the molar ratio of dilution and a higher molar ratio is preferable. However, a molar ratio of 500 may be an upper limit in practice.

The acid catalysts to be used are protonic acids, solid acids and protonic acids carried on solid acids. The protonic acids are exemplified by inorganic protonic acids such as phosphoric acid, sulfuric acid, hydrochloric acid and heteropoly-acids such as silicotungstic acid and phosphotungstic acid, and organic protonic acids such as benzenesulfonic acid and toluenesulfonic acid. The solid acids are exemplified by synthetic solid acid catalysts such as silica-alumina, silica-magnesia and zeolite; and natural solid acid substances such as activated clay, acid clay, kaolin and attapulgite. Carrier-supported catalysts in which the foregoing protonic acids are supported on inorganic porous carriers such as silica or alumina having no or slight acidic activity, can also be used.

The temperature of contact with the acid catalyst can be properly selected according to the kind of an acid catalyst and reaction phase. In general, the temperature is in the range of 200° C. to 650° C. That is, temperatures in the range of 300° C. to 600° C. are more preferable in the contact with a solid acid. Meanwhile, temperatures of 300° C. to 650° C., more preferably 350° C. to 500° C., are selected in the gaseous catalytic cracking with protonic acid catalyst.

In the process of catalytic cracking according to the present invention, 1,1-bis(p-alkylphenyl)ethane is brought into contact with the acid catalyst under the conditions of the foregoing dilution and temperature to crack the compound. Even though the method for cracking can be selected in accordance with the kind of acid catalyst, the gaseous catalytic cracking with a solid acid catalyst or a carrier supported-solid acid catalyst is desirable in view of the corrosion of reaction apparatus and the practice of continuous operation. In the gaseous catalytic cracking, any of atmospheric pressure, elevated pressure and reduced pressure can be employed so long as 1,1-bis(p-alkylphenyl)ethane is maintained in a gas phase under the diluted condition. The mode of reaction may be any of fixed bed reaction, moving bed reaction and fluidized bed reaction.

With regard to the contact time in continuous reaction, the value of SV can be selected from the range of 0.01 to 1000.

The cracking reactions in the second step are represented by chemical equations as follows. When the right side of ethylidene group is cracked:

When the left side of ethylidene group is cracked:

In the above formulae, $Ar_1$ and $Ar_2$ are benzene nuclei having an alkyl side chain.

That is, p-alkylstyrene and monoalkylbenzene are produced as cracking products.

After the cracking, the reaction mixture is cooled and separation of cracking products is carried out to recover highly pure p-alkylstyrene and monoalkylbenzene.

As the method for separation, any of conventionally known physical methods and chemical methods can be selected. Exemplified as physical methods are the separation by solvent extraction utilizing the difference in solubilities to a solvent or the difference in distribution coefficients; the separation by adsorption utilizing the difference in the liability to be adsorbed; separation by crystallization utilizing the difference in melting points or freezing points; and separation by distillation utilizing the difference in boiling points.

Among the above separation methods, the separation by distillation is preferable in practice because of its easiness in operation.

As described above, in the method of the present invention, monoalkylbenzene is firstly reacted with acetaldehyde in the presence of hydrogen fluoride catalyst to obtain 1,1-bis(p-alkylphenyl)ethane at low cost.

In the preparation using sulfuric acid catalyst, sulfonation product formed by the direct reaction of monoalkylbenzene and the catalyst causes the loss of monoalkylbenzene. However, the method of the present invention is free from such a disadvantage because hydrogen fluoride is used as a catalyst. In addition, the dilute hydrogen fluoride catalyst after the reaction can be easily recovered by distillation because the boiling point of hydrogen fluoride is as low as 19.5° C. and it can be used again for the next reaction to reduce greatly the cost for catalyst.

Furthermore, when alkylbenzene having an alkyl substituent group with less than 3 carbon atoms is used, the by-product of p-alkylethylbenzene does not cause any loss if it is dehydrogenated, as described in the foregoing passage. In the case of the use of alkylbenzene having an alkyl substituent group with 3 or more carbon atoms like the method of the present invention, the by-product of alkylethylbenzene has never been used effectively, which has been the loss of starting alkylbenzene.

According to the present invention, however, it has been made possible that the loss caused by the formation of by-product is practically reduced to a level lower than 1% relative to the starting alkylbenzene. Consequently, it is quite advantageous that the yield of 1,1-bis(p-alkylphenyl)ethane can be improved and the loss of alkylbenzene can be eliminated.

The p-isobutylstyrene as a precursor for a medicine of ibuprofen can be easily prepared by catalytically cracking 1,1-bis(p-isobutylphenyl)ethane. The p-position selectivity in the preparation of 1,1-bis(p-isobutylphenyl)ethane has been a problem because the ibuprofen is a medicine.

It was understood that in the method of the present invention, the p-position selectivity of 1,1-bis(p-isobutylphenyl)ethane is as high as more than 95%, which is superior to the case in which sulfuric acid catalyst is used.

The above advantages can be summarized such that, in the case that the monoalkylbenzene is an expensive material such as isobutylbenzene, the effect to reduce the preparation cost quite large.

In the following, the present invention will be described in more detail with reference to several experiments.

EXPERIMENT 1

To a 2 liter round bottom flask equipped with a stirrer were fed 670 g (5 moles) of isobutylbenzene (purity: above 99.8%) and 600 g (30 moles) of anhydrous hydrogen fluoride. The contents in the flask were cooled to $-20°$ C. by external cooling. A mixture of 44 g (1 mole) of acetaldehyde and 134 g (1 mole) of isobutylbenzene was dropped little by little over 4 hours with stirring and cooling at $-20°$ C. After the dropping, the stirring was continued for further 2 hours and the reaction mixture was then subjected to distillation to remove hydrogen fluoride.

Then, about 2% aqueous solution of sodium hydroxide was added to the reaction mixture to neutralize it. After the neutralization, the lower water layer was discharged. The remained oily layer was sufficiently dried and it was subjected to reduced pressure distillation to obtain 271 g of 1,1-bis(p-isobutylphenyl)ethane. The yield of this 1,1-bis(p-isobutylphenyl)ethane was 92.2% by mole on the basis of acetaldehyde and the selectivity to p-position was 96.4%. The quantity of the fraction of unreacted isobutylbenzene was 510 g (3.8 mole) and the fraction of by-product of p-isobutylethylbenzene was less than 1 g. The concentration of acetaldehyde in the reaction mixture during the addition of acetaldehyde solution was 0.5% by weight.

The quantity of anhydrous hydrogen fluoride which was recovered by distillation was 582 g (recovery rate: 97%).

EXPERIMENTS 2 to 6

Reaction was carried out in the like manner as in Experiment 1 except that the molar ratios of hydrogen fluoride to acetaldehyde were changed, thereby obtaining 1,1-bis(p-isobutylphenyl)ethane. The results are shown in the following Table 1.

EXPERIMENTS 7 to 9

Reaction was carried out in the like manner as in Experiment 6 except that the molar ratios of isobutylbenzene to acetaldehyde were changed, thereby obtaining 1,1-bis(p-isobutylphenyl)ethane. The results are shown in the following Table 2.

EXPERIMENTS 10 to 12

Reaction was carried out in the like manner as in Experiment 6 except that the reaction temperatures were changed, thereby obtaining 1,1-bis(p-isobutylphenyl)ethane. The results are shown in the following Table 3.

EXPERIMENTS 13 to 16

Reaction was carried out in the like manner as in Experiment 1 except that isobutylbenzene was replaced with other monoalkylbenzenes having an alkyl side chain with 3 or more carbon atoms, thereby obtaining 1,1-bis(p-alkylphenyl)ethanes. The results are shown in the following Table 4.

TABLE 1

| Experiment No. | 2 | 3 | 4 | 5 | 6 |
|---|---|---|---|---|---|
| Initial Feed to Flask | | | | | |
| Isobutylbenzene g (mole) | 670 (5) | 670 (5) | 670 (5) | 670 (5) | 670 (5) |
| Anhydrous Hydrogen Fluoride g (mole) | 2 (0.1) | 20 (1) | 200 (10) | 400 (20) | 1200 (60) |
| Additional Feed | | | | | |
| Isobutylbenzene g (mole) | 134 (1) | 134 (1) | 134 (1) | 134 (1) | 134 (1) |
| Acetaldehyde g (mole) | 44 (1) | 44 (1) | 44 (1) | 44 (1) | 44 (1) |
| Results | | | | | |
| BBE Yield* (mole %) | 1.0 | 4.2 | 82.1 | 88.3 | 86.0 |
| Formation of By-Product** PBE (mole %) | 5.5 | 2.7 | 0.6 | 0.3 | 0.2 |
| Distillation of Hydrogen Fluoride | | | | | |
| Recovery Rate (%) | 0 | 12 | 91 | 96 | 98 |
| Residue (g) | 5 | 46 | 57 | 50 | 51 |

Notes for the following Tables 1 to 4:
*BBE Yield: The yield of 1,1-bis(p-isobutylphenyl)-ethane (BBE) on the basis of acetaldehyde BAE Yield: The yield of 1,1-bis(p-alkylphenyl)-ethane (BAE) on the basis of acetaldehyde
**Formation of By-Produt PBE: Rate of formation of p-isobutylethylbenzene on the basis of isobutylbenzene
***Reaction Temperature: −20° C. (except Table 3)

TABLE 2

| Experiment No. | 7 | 8 | 9 |
|---|---|---|---|
| Initial Feed to Flask | | | |
| Isobutylbenzene g (mole) | 335 (2.5) | 1340 (10) | 201 (1.5) |
| Anhydrous Hydrogen Fluoride g (mole) | 1200 (60) | 1200 (60) | 1200 (60) |
| Additional Feed | | | |
| Isobutylbenzene g (mole) | 67 (0.5) | 268 (2) | 40.2 (0.3) |
| Acetaldehyde g (mole) | 44 (1) | 44 (1) | 44 (1) |
| Results | | | |
| BBE Yield* (mole %) | 82.1 | 94.7 | 66.7 |
| Formation of By-Product** PBE (mole %) | 0.8 | 0.1 | 1.6 |
| Distillation of Hydrogen Fluoride | | | |
| Recovery Rate (%) | 96 | 98 | 97 |
| Residue (g) | 62 | 46 | 50 |

TABLE 3

| Experiment No. | 10 | 11 | 12 |
|---|---|---|---|
| Reaction Temperature | 10 | −10 | −50 |
| Initial Feed to Flask | | | |
| Isobutylbenzene g (mole) | 670 (5) | 670 (5) | 670 (5) |
| Anhydrous Hydrogen Fluoride g (mole) | 1200 (60) | 1200 (60) | 1200 (60) |
| Additional Feed | | | |
| Isobutylbenzene g (mole) | 134 (1) | 134 (1) | 134 (1) |
| Acetaldehyde g (mole) | 44 (1) | 44 (1) | 44 (1) |
| Results | | | |
| BBE Yield* (mole %) | 78.3 | 83.6 | 93.5 |
| Formation of By-Product** PBE (mole %) | 0.6 | 0.3 | 0.2 |
| Distillation of Hydrogen Fluoride | | | |
| Recovery Rate (%) | 97 | 98 | 98 |
| Residue (g) | 59 | 54 | 46 |

TABLE 4

| Experiment No. | 13 | 14 | 15 | 16 |
|---|---|---|---|---|
| Monoalkyl-Benzene | n-Butylbenzene | t-Butylbenzene | 2-Methylbutylbenzene | 2,3-Dimethylbutylbenzene |
| Initial Feed to Flask | | | | |
| Monoalkylbenzene g (mole) | 670 (5) | 670 (5) | 740 (5) | 810 (5) |
| Anhydrous Hydrogen Fluoride g (mole) | 600 (30) | 600 (30) | 600 (30) | 600 (30) |
| Additional Feed | | | | |
| Monoalkylbenzene g (mole) | 134 (1) | 134 (1) | 148 (1) | 162 (1) |
| Acetaldehyde g (mole) | 44 (1) | 44 (1) | 44 (1) | 44 (1) |
| Results | | | | |
| BAE Yield* (mole %) | 91.1 | 92.6 | 91.0 | 90.6 |
| p-Position Selectivity (%) | 95.2 | 96.8 | 96.1 | 96.3 |

EXPERIMENT 17

Catalytic Cracking of 1,1-Bis(p-Isobutylphenyl)ethane

A silica-alumina catalyst N-631-L (trademark, made by Nikki Chemical Corp.) of 15 to 25 mesh in particle size was filled into a reaction tube as high as 135 mm, which reaction tube was 12 mm in inner diameter and was made of stainless steel. This was heated to 500° C. by an electric furnace. To this reaction tube were continuously fed 15 ml/hr of 1,1-bis(p-isobutylphenyl)ethane prepared in Experiment 1 and 170 ml/hr of water to to carry out catalytic cracking. After cooling the outlet of the reaction tube, an oily layer was separated and it was analyzed by gas chromatography. The results of this experiment are as follows:

| Results of Gas Chromatographic Analysis | |
|---|---|
| Components | Composition (wt. %) |
| Lighter fraction | 2.7 |
| Isobutylbenzene fraction | 24.6 |
| p-Isobutylstyrene fraction | 24.8 |
| Unreacted 1,1-bis(p-isobutyl-phenyl)ethane fraction | 44.3 |
| Others | 3.6 |
| Total | 100.0 |

EXPERIMENT 18

Catalytic Cracking of 1,1-Bis(p-Isobutylphenyl)ethane

Using a synthetic silica-alumina catalyst FCC-HA (trademark, made by Catalyst & Chemicals Industries Co., Ltd.), 1,1-bis(p-isobutylphenyl)ethane prepared in Experiment 1 was catalytically cracked in the like manner as in Experiment 17. After cooling the outlet of the reaction tube, an oily layer was separated and it was analyzed by gas chromatography. The results are shown in the following.

| Results of Gas Chromatographic Analysis | |
|---|---|
| Components | Composition (wt. %) |
| Lighter fraction | 3.1 |
| Isobutylbenzene fraction | 30.2 |
| p-Isobutylstyrene fraction | 26.7 |
| Unreacted 1,1-bis(p-isobutyl-phenyl)ethane fraction | 37.3 |
| Others | 2.7 |
| Total | 100.0 |

COMPARATIVE EXPERIMENT 1

To a 2 liter round bottom flask equipped with a stirrer were fed 670 g (5 moles) of isobutylbenzene and 600 g (5.8 moles) of sulfuric acid (95 wt. % conc.). The contents in the flask were maintained below 0° C. by external cooling. A mixture of 44 g (1 mole) of acetaldehyde and 134 g (1 mole) of isobutylbenzene was dropped little by little over 4 hours with stirring and cooling at 0° C. After the dropping, the stirring was continued for further 2 hours and the reaction mixture was left to stand still in a dropping funnel. After removing the sulfuric acid layer as the lower layer, about 2% aqueous solution of sodium hydroxide was added with shaking until the contents was neutralized. The lower water layer was then discharged and the oily layer was subjected to reduced pressure distillation to obtain 262 g of 1,1-bis(p-isobutylphenyl)ethane. The yield of this 1,1-bis(p-isobutylphenyl)ethane was 89% by mole on the basis of acetaldehyde and the selectivity to p-position was 93.5%.

The sulfonation products contained in the separated sulfuric acid layer was analyzed by NMR and ion chromatography. As a result, it was understood that the rate of formation of sulfonation product of isobutylbenzene sulfonic acid was 7.4% by mole on the basis of isobutylbenzene.

What is claimed is:

1. A method for producing p-alkylstyrene which is characterized in that monoalkylbenzene having an alkyl substituent group with 3 or more carbon atoms is reacted with acetaldehyde in the presence of hydrogen fluoride catalyst under the conditions of a temperature of 0° C. or lower, a molar ratio of 2 to 100 in "alkylbenzene/acetaldehyde" to be fed to the reaction system, the other molar ratio of 1.7 to 300 in "hydrogen fluoride/acetaldehyde" to be fed to the reaction system, the proportion of hydrogen fluoride to the sum of hydrogen fluoride and water in the reaction system of 65% by weight or higher, and the concentration of acetaldehyde in the reaction system of 1.0% by weight or lower to obtain 1,1-bis(p-alkylphenyl)ethane, and then subjecting the obtained 1,1-bis(p-alkylphenyl)ethane to catalytic cracking at a temperature in the range of 200° to 650° C. in the presence of an acid catalyst.

2. The method for producing p-alkylstyrene in claim 1, wherein isobutylbenzene is reacted with acetaldehyde to obtain 1,1-bis(p-isobutylphenyl)ethane and said 1,1-bis(p-isobutylphenyl)ethane is catalytically cracked in the presence of an acid catalyst.

3. The method for producing p-alkylstyrene in claim 1, wherein monoalkylbenzene is reacted with acetaldehyde under the conditions that said molar ratio of "alkylbenzene/acetaldehyde" to be fed to the reaction system is 2.2 to 50, said the other molar ratio of "hydrogen fluoride/acetaldehyde" to be fed to the reaction system is 2.7 to 100, the proportion of hydrogen fluoride to the sum of hydrogen fluoride and water in the reaction system is 75% by weight or higher, and the concentration of acetaldehyde in the reaction system is 0.5% by weight or lower.

4. The method for producing p-alkylstyrene in claim 1, wherein said acid catalyst is one member selected from the group consisting of protonic acids, solid acids and protonic acids carried on solid acids.

5. The method for producing p-alkylstyrene in claim 4, wherein catalytic cracking is carried out in a gas phase in the presence of a solid acid and/or a protonic acid carried on a solid acid.

6. The method for producing p-alkylstyrene in claim 1, wherein said catalytic cracking is carried out by diluting 1,1-bis(p-alkylphenyl)ethane by adding an inert gas so that the molar ratio as represented by "inert gas/1,1-bis(p-alkylphenyl)ethane" is 50 or higher.

* * * * *